United States Patent [19]

Kreh et al.

[11] Patent Number: 4,647,349

[45] Date of Patent: Mar. 3, 1987

[54] OXIDATION OF ORGANIC COMPOUNDS USING CERIC IONS IN AQUEOUS TRIFLUOROMETHANESULFONIC ACID

[75] Inventors: Robert P. Kreh, Jessup; Robert M. Spotnitz, Catonsville, both of Md.

[73] Assignee: W. R. Grace & Co., New York, N.Y.

[21] Appl. No.: 859,565

[22] Filed: May 5, 1986

[51] Int. Cl.$^4$ ................................................ C25B 3/02
[52] U.S. Cl. .................................... 204/59 R; 204/78; 260/396 R; 260/385; 568/309; 568/426
[58] Field of Search .............. 204/59 R, 78; 568/309, 568/426; 260/385, 369 R

[56] References Cited

U.S. PATENT DOCUMENTS

| | | | |
|---|---|---|---|
| 3,486,992 | 12/1969 | Frye | 204/78 |
| 3,873,580 | 3/1975 | Rennie | 568/309 |
| 4,312,721 | 1/1982 | Oehr | 204/78 |
| 4,354,904 | 10/1982 | Malloy et al. | 204/59 R |
| 4,371,431 | 2/1983 | Switzer | 204/59 R |
| 4,482,438 | 11/1984 | Ballard et al. | 204/78 |
| 4,560,804 | 12/1985 | Yeh et al. | 568/309 |
| 4,582,942 | 4/1986 | Comninellis et al. | 568/426 |

FOREIGN PATENT DOCUMENTS 1132996  5/1982  Canada.

OTHER PUBLICATIONS

Marrocco et al., J. Org. Chem. 48 (1983), pp. 1487–1491.

*Primary Examiner*—Arthur P. Demers
*Attorney, Agent, or Firm*—Howard J. Troffkin

[57] ABSTRACT

A process for oxidizing aromatic and alkyl substituted aromatic compounds to carbonyl containing compounds by contacting an aromatic and alkyl aromatic compound with an aqueous solution of ceric trifluoromethanesulfonate having from at least 0.75 to 7 molar concentration of free acid of trifluoromethanesulfonic acid and at least 0.2 molar cerium ion concentration. The present process provides a highly effective means of forming the desired carbonyl containing product in good yields and high selectivity.

21 Claims, No Drawings

OXIDATION OF ORGANIC COMPOUNDS USING CERIC IONS IN AQUEOUS TRIFLUOROMETHANESULFONIC ACID

BACKGROUND OF THE INVENTION

The present invention is directed to an improved electrochemical oxidation process for forming quinones and aromatic aldehydes or ketones from corresponding aromatic and alkyl aromatic compounds in good yields and high selectivity. More specifically, the invention described and claimed herein requires the use of a strong aqueous trifluoromethanesulfonic acid solution having high concentrations of ceric trifluoromethanesulfonate dissolved therein.

The quinones and aromatic aldehydes or ketones obtainable by the present process have a wide variety of known utility. For example, the quinones, such as naphthoquinone, are known additives in the paper making industry. The aldehydes, such as benzaldehyde, tolualdehyde and the like, and ketones such as p-methylacetophenone are known intermediates used in forming fragrance components useful in perfumes and colognes. Certain aldehydes and ketones have been used in forming pharmaceuticals.

The products achieved by the present invention have been previously formed by a variety of processes which may be generally classified as chemical or electrochemical. For example, aromatic aldehydes have been chemically formed by air oxidation conducted in an oxygen enriched environment at high temperatures and pressure in the presence of a transition metal catalyst or by using known chemical oxidizing agents which are not regenerable. Oxidation has also been achieved by direct electrochemical oxidation of aromatic compounds in the presence of dilute acid electrolytic solutions as described in U.S. Pat. Nos. 4,298,438 and 4,354,904 and by indirect electrochemical oxidation in which the oxidant is electrolytically generated and, in turn, used to oxidize the aromatic compound.

Compounds which are known to be capable of acting as an indirect oxidant include transition metal salts, particularly the metals of cobalt, chromium, manganese, iron, lead, silver and cerium. Because regeneration of the spent metal to its higher oxidation state is not always highly effective and/or other insoluble salts, such as oxides, etc., are formed, those skilled in this art tend to use the salts of chromium, manganese, cobalt, iron or lead as these salts are less expensive and replacement of spent materials do not greatly detract from the economics of the process. However, each of these metal ion oxidants have certain properties which cause them to make the oxidation process ineffective. For example, chromium ions give poor selectivity towards the desired products, cerium and manganese salts are believed to have low solubility of the oxidized and/or reduced ions in acidic solutions, the higher oxidation states of silver, cobalt and lead ions are not very stable and, in the case of iron, is not very reactive. Indirect electrochemical oxidation has been further complicated by the properties of the anion specie present. For example, certain anions (e.g., chloride, nitrate, perchlorate) are highly reactive with the organic substrate producing by-products or conditions which preclude their use on a commercial scale. Other less reactive anions (e.g., sulfate, acetate, fluoride, boron fluoride, silicon fluoride) generally form salts of low solubility, inhibit the rate of reaction of the oxidant with the organic substrate and/or inhibit the ability of the spent oxidant to be regenerated. In addition, certain organic acid salts (e.g., benzenesulfonate) have been found to be insufficiently stable to be useful in an indirect oxidation process.

Cerium and its ceric ion is a well known oxidizing agent in organic chemistry. It has the potential of presenting an excellent one electron oxidant but has not been previously used extensively or on an industrial scale because of the inability of both the ceric and cerous ions to be maintained in solution at high concentrations and under high acidity causing its use to be limited to slurries or very low concentrations. In addition, ceric oxidant has been associated with poor reactivity and selectivity. The cerium salts are prohibitively expensive and must, therefore, be capable of being stable, react with the organic substrate cleanly and be easily regenerated to its higher valence state. This requires the ceric salt to exhibit a high degree of stability and solubility in the electrolyte solution and be capable of achieving good reaction rates. In addition, the cerous ion must also be highly soluble to be capable of being regenerated to the ceric ion under conditions of high current efficiency at the anodic portion of the electrochemical cell. However, conditions (i.e. high acidity) preferred for best utilization of the ceric ion have previously been believed as being counterproductive to achieving proper conditions for cerous salt utilization. Therefore, it has heretofore been believed necessary to use the cerium salt at very low concentrations and under a very narrow set of conditions including those which could not demonstrate the potential necessary to provide an effective industrially suitable process.

Canadian Pat. No. 1,132,996 to Oehr describes a process for oxidizing naphthalene to naphthaquinone using ceric sulfate in dilute sulfuric acid. Both cerous sulfate and ceric sulfate are known to have low solubility in dilute acid [Solubilities of Inorganic and Organic Compounds, Vol. 3, Part I, Ed. by H. L. Silcock (1974)] and the solubility decreases with increasing acid concentration. The solubility limitations lead to the use of inefficient slurry conditions or to the need for large volumes of solution to oxidize small quantities of the organic compound. Similar problems are encountered with other salts of low solubility.

European Patent Application No. 0075828 of Mayeda et al describes a process for oxidizing fused ring compounds to their respective quinones using ceric nitrate in dilute nitric acid. Although solubility does not present a problem, the nitrate anion is known to react with the organic reactant forming nitrogen containing by-products which are difficult to handle and remove. Cerium salt solutions containing perchlorate anions have also been disclosed as a useful oxidant [Prospects for the Indirect Electrolytic Oxidation of Organics, by N. Ibl et al., AIChE Symposium Series, Electroorganic Synthesis Technology, Pg. 45, (1979)] but it is well known that the perchlorate reacts explosively with organic materials and, therefore, is unsuitable for commercial scale processes.

M. Marrocco et al [J. Org. Chem., Vol. 48, No. 9, Pg. 1487 (1983)] conducted a study of the oxidation of an organic substrate by various cerium salts in different acid electrolytes. Each of the cerium salt systems contained cerium ions maintained at very low concentrations. Even at the low concentrations, many of the systems were slurries and the conversion and selectivity were low.

It must be understood that although cerous/ceric ions have been known and used in oxidation reactions, there is a need to have a system wherein the ceric oxidant can be sufficiently stable under oxidizing conditions to be useful in indirect electrochemical processes, to be capable of undergoing repeated cycling between its cerous ($Ce^{+3}$) and ceric ($Ce^{+4}$) species in a high degree of efficiency under the reaction and electrolysis conditions, to be highly selective in forming the desired carbonyl group containing compounds, to be capable of exhibiting high reaction rates to make the process attractive on a commercial scale, to have high solubility to aid in the efficiency of the reaction and to eliminate the problems associated with slurries of cerium salts. It is readily seen that a means of achieving this combination of desired properties would aid in providing a process which would find a high degree of acceptance in electrochemical oxidation of aromatic and alkyl substituted aromatic compounds.

SUMMARY OF THE INVENTION

The present invention is directed to an electrochemical process wherein ceric ions are generated and used as an oxidant to transform aromatic and alkyl substituted aromatic compounds to carbonyl containing compounds in good selectivity. The present process requires the utilization of at least 0.2 molar concentration of cerium salts of trifluoromethanesulfonic acid dissolved in a highly acidic aqueous solution containing substantial excess of the free trifluoromethanesulfonic acid. The highly acidic cerium salt solution, as described hereinbelow, exhibits the desired combination of properties (stability, solubility, reactivity, capability to achieve high current density, capability of repeated cycling between cerous and ceric, and selectivity of product formation) to provide a commercially attractive process.

DETAILED DESCRIPTION OF THE INVENTION

The present invention is directed to a process for selectively forming carbonyl containing compounds from respective aromatic compounds.

Certain terms used in the present specification and in the appended claims are defined herein below to aid in providing a clear description of the invention:

The term "aromatic" shall, unless specifically indicated otherwise, refer to benzylic and fused benzylic compounds such as benzene, naphthalene, anthracene and the like. The compounds may be unsubstituted or may contain substitution groups which are inert to oxidation such as halides, alkoxy, nitro, sulfonyl, amide, tertiary amino, tertiary alkyl and carboxylate ester groups.

The term "alkyl aromatic" refers to $C_1$-$C_6$ alkyl substituted benzylic and fused benzylic compounds. The compounds shall contain one or more than one primary or secondary $C_1$-$C_6$ alkyl group attached to the aromatic ring and may, in addition, contain groups which are inert to oxidation such as halides, alkoxy, nitro, sulfonyl, amido, tertiary amino, tertiary alkyl, and carboxylic ester groups. Examples of such compounds include toluene, (o, m or p) xylene, trimethylbenzene, (o, m or p) ethyltoluene, (o, m or p) propyltoluene, (o, m or p) methoxyethylbenzene, (o, m or p) ethoxyethylbenzene, 1, 2 dimethylnaphthalene, (o, m or p) methyl-N,N-dimethylaniline (o,m or p) chlorotoluene and the like.

The term "indirect electrochemical oxidation" refers to an oxidation of an aromatic or alkyl aromatic compound which proceeds in two steps such that the first step provides a metal ion oxidant (e.g. $Ce^{+4}$) by anodic charge exchange and the second step comprises the reacting of the metal ion oxidant with an aromatic or alkyl aromatic compound to produce carbonyl containing compounds. The oxidation of the aromatic or alkyl aromatic compound does not occur selectively in the absence of the metal ion oxidant. The indirect electrochemical oxidation of the organic substrate can be conducted in the electrochemical reactor (in-cell) or in a separate reactor (ex-cell).

The terms "cerous", "ceric" and "cerium" refer, respectively, to the cerium ion or salt of a cerium ion in its lower valence state (+3), its higher valence state (+4) and as a mixture of both lower and higher valence state species.

The present invention provides an improved indirect electrochemical oxidation process. The improvement requires the utilization of cerium salts of trifluoromethanesulfonic acid present in concentration of at least 0.2 molarity in solution in trifluoromethanesulfonic acid of 0.75 to 7 Normality to provide efficient reaction rates for oxidizing the organic substrate and high current efficiency to regenerate the oxidant.

As discussed above, certain salts have anions which have detrimental effects on the system or the salt, in either its oxidized or reduced form or in combination, has low solubility in strong acid solutions. For example, cerium sulfates are known to have low solubility in weak acidic solutions and their solubility decreases with increase in acidity.

It has now been unexpectedly found that cerium trifluoromethanesulfonates can be used as an effective oxidant for indirect electrochemical synthesis when used according to the present invention which requires the solution to contain at least 0.75 and preferably at least 1.5 Normal free acid in the solution, to have the cerium salts substantially completely dissolved in the solution and the combined cerium ion concentration to be at least 0.2 molar. The utilization of the presently required solution unexpectedly provides the combination of advantages of:

(1) high solubility of both the cerous and the ceric ions over a wide acid concentration provided the required minimum acid concentration is maintained;

(2) high current efficiency at high current density (of at least about 75 mA/cm$^2$ or greater) to provide effective anodic oxidation of the cerous ions to ceric ions;

(3) fast reaction rate of the ceric oxidant with the organic reactant;

(4) high selectivity of the oxidation of the organic reactant to formation of desired carbonyl containing compounds;

(5) passivity of the anion and the free acid to the organic reactant and to the electrodes of the cell; and (6) clean, uncomplicated reduction at the cathode to again aid in effecting an efficient process.

The subject process requires the use of the salts of cerium trifluoromethanesulfonate. Solutions of the salts can be readily formed by reacting a cerous salt of an inorganic acid with aqueous trifluoromethanesulfonic acid. The resulting aqueous solution should, preferably, be substantially free of extraneous anions of other acids such as sulfates, nitrate, perchlorate, halide, acetate, trifluoroacetate and the like except that methanesulfonic acid and trifluoromethanesulfonic acid shall not be considered extraneous ions. It is preferred that the concentration of such extraneous anions be maintained at a low value of from 0 to 0.5 preferably from 0 to 0.1 mole per mole of cerium ions present in the solution. It is therefore most desired to form the subject salts from cerous carbonate, cerium dioxide and the like and most preferably from cerous carbonate. When other acid salts are used, their anions should be substantially removed from the solution by known means prior to using solution in the subject process. For example, if sulfate ions are present they can be removed by precipitation with lead(II) carbonate. Similarly, chloride ions can be removed by treating the solution with silver carbonate. Other extraneous ions can be removed in similar manners known in the art.

As discussed above, various cerium salts have been proposed as an oxidant in electrochemical oxidation processes. The salts have been either formed from reactive anions or from a more passive anion in which case the salt is normally present in the form of a slurry or as a very dilute solution due to solubility restrictions attributable to either one or both metal ions (e.g. Ce+3, Ce+4) salt form specie. The present invention unexpectedly provides a means of maintaining high concentrations of both the ceric and cerous species in solution and thus permits cyclical formation of the cerium ions without formation of insoluble material. The present process requires the electrolytic solution to contain free trifluoromethanesulfonic acid in at least 0.75 molar concentration, normally from 1.5 to 7 molar, preferably from 1.5 to 6 molar and most preferably from 2 to 5 molar concentration. Further, it is preferable that the electrolytic solution be substantially free of inorganic acids although small amounts may be present.

The ceric and cerous salts can be dissolved in the presently described solution at high concentrations without causing precipitation of either one of the salt species. The solution can have a combined concentration of ceric and cerous metal ions at levels of 0.2 molar or greater under the process temperature conditions. Cerium concentrations of 0.5 molar and greater can be achieved when the preferred electrolytic solutions are used. It is realized that under the present process, the cerium ions can be maintained in solution at concentrations which are higher or less than the above stated concentrations provided they are maintained in solution. The specific concentration which meet economic, process and solubility restraints can be readily determined by conventional techniques.

The present process further provides a means of readily converting certain aromatic and alkyl aromatic compounds to their corresponding carbonyl containing compound which was either difficult or impractical to accomplish by prior use of ceric salts. This ability is probably due to a combination of factors (although not meant to be a limitation of the present invention) capable of being used under the present invention. For example, the ability to maintain high acid normality of the solution may enhance oxidizing certain organic substrates. The high concentration of the oxidant in solution may catalyze the conversion of certain organic substrates to desired carbonyl containing compounds.

The aqueous solution may contain an organic co-solvent which can aid in solvating the aromatic or alkyl aromatic reactant. The co-solvent may be miscible or immiscible with the aqueous phase. Such co-solvents may be any which is inert in the system as are well known and include lower alkyl alcohols such as methanol, ethanol, isopropanol and the like, acetonitrile and the like. Other conventional materials may be added to the system provided they are inert to the cerium salt and free acid used herein. Examples of such materials include anionic surfactants such as sodium dodecylbenzene sulfonate and the like and cationic surfactants such as tetrabutylammonium hydroxide and the like.

The generation and subsequent regeneration of ceric oxidant can be readily carried out by supplying the solution of the present invention to an electrolytic cell in either a batch or continuous manner. The cell may be either undivided or divided by a porous partition wall or membrane between electrodes. The electrodes may be of any suitable form such as plates, lattices, expanded metal, or reticulated porous material and the like. The anode may be any of the known materials suitable for preforming the metal-ion oxidation and are, preferably selected from lead, lead oxide, platinum, platinized titanium, platinized niobium or metal oxide-titanium composite. The cathode of the cell may be any of the known materials suitable for performing reductions in the aqueous-acid solutions with or without the presence of metal ions such as, for example, steel, copper, and nickel. The use of the presently described cerium salt solution has, as one of its unexpected properties, the ability to readily and effectively generate and regenerate ceric oxidant from cerous ions at high current density. Another unexpected property is the ability of the solution to cause a clean cathodic reduction without production of by-products which detract from the process and require separation therefrom. The electrolysis can be performed at voltages ranging from about 2 to 20 volts with current density ranging between about 0.1 to about 500 mA/cm$^2$, preferably from 10 to 400 mA/cm$^2$ and most preferably from 70 to 300 mA/cm$^2$ (based on electrode area excluding roughness factor). The electrolysis may be conducted at a temperature of from about $-20°$ to 150° C. and preferably from 0° to 100° C. It is most preferable to have the cell temperature and the reaction temperature (where the cell and chemical reactor are separate) be substantially the same.

The organic compounds which can be effectively oxidized using the solution of the present process are aromatic and alkyl aromatic compounds. The aromatic compounds include benzylic and fused benzylic ring compounds which may be unsubstituted or be substituted with a group which is substantially inert to oxidation. Examples of such compounds include benzene, naphthalene, anthracene and the like as well as such compounds which contain groups attached to the ring which are inert to the present indirect oxidation. Such groups can be readily determined by simple laboratory testing and include ($C_1$–$C_4$) alkoxy, tert-alkyl ($C_4$–$C_7$), phenoxy, nitro, tertiary amino, sulfonyl, amido, and carboxylic acid ester groups and the like. The alkyl substituted aromatic compounds include the above defined aromatic compounds which further contains at least one primary alkyl or secondary alkyl group or both.

The organic compounds described above are oxidized to their respective carbonyl containing compounds by contacting the organic compound with the acidic aqueous solution described above which contains the oxidant, ceric trifluoromethanesulfonate. The contacting of the oxidant and the organic compound may be conducted directly within the electrolytic cell. However, it is preferable to transfer the subject oxidant containing solution to a separate reactor vessel where it is contacted with the organic compound to be oxidized under agitation. The organic compound can be introduced to the reactor either dissolved or dispersed in the aqueous phase or dissolved in a co-solvent with the aqueous solution.

It has been unexpectedly found that the solution used in the present process is capable of providing ceric ions in high concentration and at high solubility in the liquid phase to provide high reaction rate in oxidizing the organic compound. In addition, the subject process unexpectedly provides a means for readily and selectively forming quinones (from aromatic compounds) and aldehydes or ketones (from alkyl aromatics) without substantial by-product formation. When the organic compound is present in excess, such as from about three to ten fold excess of stoichiometry, one will form alcohol as well as the above quinone, aldehyde or ketone.

The organic oxidation can be carried out under ambient temperature and pressure conditions. The temperature may be varied from about 0° to about 100° C. with from 20° to 75° C. being preferred. The pressure may be elevated or reduced for process reasons.

The solution removed from the reaction zone contains product and spent metal ion oxidant (cerous). The product can be readily separated from the solution by phase-separation, distillation, precipitation or extraction with an appropriate solvent such as dichloroalkanes, cyclohexane and the like. The particular mode of separation will depend upon the identity of the product formed and can be readily ascertained by the artisan.

The resultant solution (after separation of the product) will contain cerous salt as the sole or major component and may contain small amounts of unreacted ceric salt. This solution can be returned to the electrolytic cell for regeneration of the ceric ion oxidant. It has been found that the ceric/cerous salts used herein readily regenerate a multiplicity of cycles without formation of by-products which have detrimental effect on the efficiency of the process.

The following example is given for illustrative purposes only and is not meant to be a limitation on the present invention as defined by the claims appended hereto. All parts and percentages are by weight unless otherwise indicated.

EXAMPLE I 100 parts of trifluoromethanesulfonic was mixed with 23 parts cerous carbonate (obtained as the pentahydrate) in a small quantity of water. The resultant clear solution was diluted up with addition of water to provide a 0.55 M cerous trifluoromethanesulfonate in 2.8 M trifluoromethanesulfonic acid aqueous solution. 150 parts of the solution was charged to the anodic compartment of a plate and frame type electrolytic cell. The anode was a platinum-clad niobium expanded mesh having both surfaces coated with 63.5 micrometer of platinum (total surface area of ca. 240 cm$^2$). The anolyte compartment was separated from the catholyte compartment by a commerical perfluorinated ion exchange membrane (Nafion 390). The anolyte compartment was maintained at a temperature of 50° while a constant current of 11 amps was maintained to yield 0.38 M Ce(IV) trifluoromethanesulfonate after passage of 1F/mole of charge. The current efficiency was 76%.

The cerium salts were at concentrations where no precipitation was observed. 1.25 parts by volume of toluene was added to 120 parts by volume of the above solution derived from the electrolytic cell. The solution was stirred for 40 minutes at 25° C. under a nitrogen atmosphere. The resultant colorless solution was cooled to 0°–10° C. and extracted with methylene chloride and analyzed by gas chromatography. The toluene conversion was 94% and the selectivity to benzaldehyde was 80%.

We claim:

1. A process for forming carbonyl group containing compounds from their respective organic substrate selected from aromatic and alkylaromatic compounds comprising contacting the organic substrate with an aqueous solution containing ceric trifluoromethanesulfonate.

2. The process of claim 1 wherein said solution contains at least 0.75 molar concentration of free trifluoromethanesulfonic acid, said solution being substantially free of extraneous acid anions and having at least 0.2 molar cerium concentration.

3. The process of claim 2 wherein the free acid concentration is from 1 to 7 molar and the cerium trifluoromethanesulfonate salts are dissolved in said solution.

4. The process of claim 3 wherein the solution has a concentration of extraneous anions of from 0 to about 0.5 mole per mole of cerium ions present.

5. The process of claim 3 wherein the organic substrate and ceric salt solution are contacted at a temperature ranging from 0° to 100° C.

6. The process of claim 4 wherein the organic substrate and ceric salt solution are contacted at a temperature ranging from 0° to 100° C.

7. The process of claim 3 wherein the free acid concentration is from 1.5 to 6.

8. The process of claim 4 wherein the free acid concentration is from 1.5 to 6 and extraneous anions are present in a concentration of from 0 to about 0.1 mole per mole of cerium ions present.

9. The process of claim 2 wherein the aqueous solution further contains an organic solvent for the organic substrate, said organic solvent being miscible in the aqueous solution.

10. The process of claim 2 wherein the organic substrate is introduced as a solution in an organic solvent.

11. The process of claim 2 wherein the aqueous solution contains a mixture of trifluoromethanesulfonic acid and methanesulfonic acid.

12. An indirect electrochemical oxidation process to oxidize aromatic and alkyl aromatic compounds comprising
    (a) contacting an aromatic or alkyl aromatic compound with an aqueous solution containing ceric trifluoromethanesulfonate and having having at least 0.75 molar concentration of free trifluoromethanesulfonic acid therein, said solution having all ceric and cerous ions dissolved in said solution and at a concentration of at least 0.2 molar;
    (b) separating and recovering the carbonyl containing product from the solution to yield a spent solution rich in cerous salts;
    (c) transferring the spent solution to an electrochemical cell to cause regeneration of a solution rich in the ceric salt; and
    (d) repeating steps (a), (b) and (c).

13. The process of claim 12 wherein step (a) is conducted at a temperature of from about 0° C. to 100° C. and the electrolysis of step (c) is conducted at a voltage ranging from about 2 to 20 volts with a current density of from 10 to 400 mA/cm$_2$.

14. The process of claim 12 wherein the solution has a concentration of extraneous anions of from 0 to about 0.5 mole per mole of cerium ions present.

15. The process of claim 13 wherein the solution has a concentration of extraneous anions of from 0 to about 0.5 mole per mole of cerium ions present.

16. The process of claim 12 wherein the aqueous solution further contains an organic solvent for the organic substrate, said organic solvent being miscible in the aqueous solution.

17. The process of claim 12 wherein the organic substrate is introduced as a solution in an organic solvent.

18. The process of claim 12 wherein the aqueous solution contains a surfactant.

19. The process of claim 12 wherein the oxidation is performed in the electrochemical cell.

20. The process of claim 12 wherein the aqueous solution contains a mixture of trifluoromethanesulfonic acid and methanesulfonic acid.

21. The process of claim 12 wherein the solution contains an alkyl aromatic compound in from about three to about 10 times the stoichiometric equivalence of the cerium present.

* * * * *